US006858020B2

(12) United States Patent
Rusnak

(10) Patent No.: US 6,858,020 B2
(45) Date of Patent: Feb. 22, 2005

(54) VACCINATOR DEVICE

(75) Inventor: Christopher Rusnak, Des Plaines, IL (US)

(73) Assignee: Ideal Instrument, Inc., Schiller Park, IL (US)

( * ) Notice: Subject to any disclaimer, the term of this patent is extended or adjusted under 35 U.S.C. 154(b) by 280 days.

(21) Appl. No.: 10/191,147

(22) Filed: Jul. 8, 2002

(65) Prior Publication Data

US 2004/0006309 A1 Jan. 8, 2004

(51) Int. Cl.[7] ............................................... A61M 37/00
(52) U.S. Cl. ....................................... 604/131; 604/246
(58) Field of Search ......................... 604/131, 134–136, 604/152, 154, 155–157, 187, 192, 207, 218, 246–249; 222/52, 64–66, 638, 639; 119/650, 665; 137/599.07, 909; 239/585.1

(56) References Cited

U.S. PATENT DOCUMENTS 2,512,882 A 6/1950 Truesdale
3,964,481 A 6/1976 Gourlandt et al.
4,435,173 A * 3/1984 Siposs et al. ............... 604/155
4,715,853 A 12/1987 Prindle
4,990,135 A 2/1991 Truesdale, Jr.
5,056,464 A 10/1991 Lewis
5,136,979 A 8/1992 Paul et al.
5,158,038 A 10/1992 Sheeks et al.
5,242,388 A 9/1993 Marshall, Sr.
5,438,954 A 8/1995 Phelps et al.
5,468,227 A 11/1995 Haskell
RE35,973 E 12/1998 Paul et al.
6,032,612 A 3/2000 Williams

* cited by examiner

*Primary Examiner*—Nicholas D. Lucchesi
*Assistant Examiner*—Catherine S. Williams
(74) *Attorney, Agent, or Firm*—Ian C. McLeod

(57) ABSTRACT

An automatic repeater vaccinator apparatus (10) for dispensing a predetermined volume of a fluid into an animal, particularly a fluid which is a vaccine, and reloading after each volume of fluid is dispensed. The apparatus (10) comprises a handheld syringe (100) for dispensing the fluid, a flexible conduit (12) for transferring the fluid from a dispensing means to the syringe (100), and a reservoir (48) for providing the fluid to the dispensing means. The dispensing means is electrically activated by a magnetically closeable switch (preferably a reed switch (142)) in the syringe (100), which enables a predetermined volume of the fluid to be dispensed from the syringe (100) when the dispensing means is activated and reloading fluid from the reservoir (48) to replace the volume of fluid which has been dispensed from the syringe (100) when the dispensing means is deactivated. Preferably, the dispensing means comprises a pump (200 or 500) operated by a linear actuator such as a solenoid (300), which is electrically activated by the magnetically closeable switch in the syringe (100). The apparatus (10) is particularly useful for inoculating poultry, particularly inoculating the poultry by the wing web method using the needle and hub assembly (400) which comprises the filament (402) to prevent leakage between inoculations.

16 Claims, 8 Drawing Sheets

VACCINATOR DEVICE

CROSS-REFERENCE TO RELATED APPLICATION

Not applicable.

STATEMENT REGARDING FEDERALLY SPONSORED RESEARCH OR DEVELOPMENT

Not applicable.

Reference to a "Computer Listing Appendix Submitted on a Compact Disc"

Not Applicable.

BACKGROUND OF THE INVENTION

(1) Field of the Invention

The present invention relates to an automatic repeater vaccinator apparatus for dispensing into an animal a predetermined volume of a fluid, in particular a fluid which is a vaccine, and reloading after each volume of fluid is dispensed. The apparatus comprises a handheld syringe for dispensing the fluid, a flexible conduit for transferring the fluid from a dispensing means to the syringe, and a reservoir for providing the fluid to the dispensing means. The dispensing means is electrically activated by a magnetically closeable switch (preferably a reed switch) in the syringe, which enables a predetermined volume of the fluid to be dispensed from the syringe when the dispensing means is activated and reloading fluid from the reservoir to replace the volume of fluid which has been dispensed from the syringe when the dispensing means is deactivated. Preferably, the dispensing means comprises a pump operated by a linear actuator such as a solenoid, which is electrically activated by the magnetically closeable switch in the syringe. The apparatus is particularly useful for inoculating poultry, particularly inoculating the poultry by the wing web method using the needle and hub assembly which comprises the filament to prevent leakage between inoculations.

(2) Description of Related Art

Vaccination of poultry has played an increasingly important role in the poultry industry, particularly since the advent of large-scale poultry operations which continuously raise poultry flocks one after an other without any down time between flocks to sanitize the facilities for raising the flocks. Because production of poultry is on such a large scale and the margin for profit on a per bird basis is so thin, there has been considerable interest in vaccination methods which reduce the time and cost of vaccinating poultry.

Traditionally, chicks are vaccinated by filling a handheld syringe with multiple doses of the vaccine, picking up a chick, and manually injecting the appropriate dose of vaccine into the chick. Because the entire vaccination process is manual and a large number of chicks must be vaccinated within a short period of time, the dose received by the chicks can be variable because of leakage of vaccine from the needle and miscalculation. To ensure that the chicks have received enough vaccine, the tendency is to over vaccinate the chicks, which increases the vaccine cost per chick. In addition, the handheld syringe holds only a limited number of doses which requires refilling the syringe multiple times throughout the vaccination process. Furthermore, because the distance the needle is inserted into the chick is determined by eye, for a number of chicks the needle will either be not inserted deep enough into the chick or will be inserted to deep which can kill the chick. To overcome the problems associated with manual vaccination methods, alternative vaccination methods have been developed.

Automatic egg vaccinators such as those disclosed in U.S. Pat. No. 5,158,038 to Sheeks et al., U.S. Pat. No. 5,056,464 to Lewis, U.S. Pat. No. Re. 35,973 and U.S. Pat. No. 5,136,979, both to Paul et al., U.S. Pat. No. 5,438,954 to Phelps et al., and U.S. Pat. No. 6,032,612 to Williams have been developed. While egg vaccinators are useful for some vaccine formulations such as Marek's disease vaccines, egg vaccinators are not useful for other vaccines such as Newcastle vaccines where maternal antibodies may negate the efficacy of the vaccine. Therefore, even though automatic egg vaccinators are available, the most common method for vaccinating poultry remains vaccinating new-born chicks or young chicks by hand.

Thus, a variety of methods for reducing the time and cost of vaccinating new-born chicks have been developed. For example, U.S. Pat. No. 5,468,227 to Haskell discloses an apparatus for wing-web vaccination of new-born or young chicks. To operate the apparatus, the operator places a chick in a trough in the apparatus, extends the chick's wing into a recess in the apparatus, and activates a power switch. The power switch simultaneously activates a solenoid which pushes a needle into the chick's wing web and activates a peristaltic pump which pumps vaccine from a reservoir to the needle and discharging therefrom into the wing web. As the pump shaft rotates, a pin wheel attached to a shaft connected to the pump contacts a micro-switch which breaks the circuit thereby terminating flow of the vaccine and causing retraction of the needle.

U.S. Pat. No. 3,964,481 to Gourlandt et al. discloses an apparatus for vaccinating animals including chicks. To operate the apparatus, the operator places the animal over an aperture in a retention plate of the apparatus and activates a switch which causes a needle afixed to a syringe driven by a piston operated by an electromagnet motor to extend a predetermined distance through the aperture and into the animal. When the needle has reached its predetermined distance, the piston further advances which causes a predetermined dose of vaccine to be dispensed into the animal and the electromagnet to be deactivated. A spring causes the piston to retract which during retraction creates a suction in the syringe which causes vaccine to be drawn into the syringe from a reservoir to replace the vaccine which had been dispensed.

U.S. Pat. No. 5,242,388 to Marshall, Sr. discloses an apparatus for operating a needle to inoculate the wing web of a bird. An arm rocks a needle holder back and forth between a serum container and web positioner, along a path which causes the needle holder to move substantially vertically into and out of the container and web positioner. Gears cause the needle holder to pivot on the arm in response to pivotal movement of the arm, so that the needle points downwardly throughout its movement.

While the above apparatuses have been useful, they are stationary devices which require the animal or chick to be placed into or held against the apparatus. It would be more convenient to have a handheld vaccinator but without the disadvantages of the traditional handheld syringe. To that end, U.S. Pat. No. 2,512,882 to Truesdale and U.S. Pat. No. 4,990,135 to Truesdale, Jr. disclose a repeater vaccinator for wing web inoculations comprising a syringe with a reservoir and a reciprocable needle having a portion movable into and out of the reservoir by action of a manually operated plunger. The needle has slots on either side or opening therethrough which are designed to positively attract and hold a predetermined dose of vaccine. In the rest position, the needle resides in the reservoir. When the syringe is placed against the wing web and the plunger is manually pressed, the needle exits the reservoir carrying with it the predetermined dose of vaccine and enters the wing web where the vaccine is deposited. Releasing the plunger causes the needle to retract back into the reservoir. The number doses contained within the vaccinator is limited by the size of the reservoir.

A back-fill repeater syringe which can be attached by a flexible conduit to a reservoir remote to the syringe is disclosed in U.S. Pat. No. 4,715,853 to Prindle. The syringe is manually operated by inserting the needle into an animal and pressing the head of the syringe against the animal which causes a plunger in the syringe to move forward to dispense a predetermined dose of vaccine in the syringe through the needle into the animal. Removing the needle from the animal causes the plunger to retract which draws vaccine from the reservoir to replace the dose of vaccine that had been dispensed.

While the handheld repeater syringes have been beneficial, they are manual in that they require constant hand motion to dispense the vaccine which causes operator fatigue and can lead to occupational diseases such as carpel tunnel syndrome. Therefore, there is a need for a handheld repeater syringe that does not require continual hand motion to dispense the vaccine.

SUMMARY OF THE INVENTION

The present invention provides an automatic repeater vaccinator apparatus for dispensing predetermined volumes of a fluid such as vaccine and reloading after each volume of fluid is dispensed. The apparatus comprises a handheld syringe for dispensing the fluid, a flexible conduit for transferring the fluid from a dispensing means to the syringe, and a reservoir for providing the fluid to the dispensing means. The dispensing means is electrically activated by a magnetically closeable switch preferably a magnetically closeable reed switch) in the syringe, which enables a predetermined volume of the fluid to be dispensed from the syringe when the dispensing means is activated and reloading fluid from the reservoir to replace the volume of fluid which has been dispensed from the syringe when the dispensing means is deactivated. Preferably, the dispensing means comprises a pump operated by a linear actuator or solenoid.

Therefore, the present invention provides an improved handheld syringe assembly which electrically connects to an electrically powered dispensing means which reloads a liquid to be dispensed through a conduit to the syringe assembly through a disposable needle and hub assembly or hub, either mounted on a body of the syringe assembly, after injecting a dose of the liquid which comprises (a) a permanent magnet mounted on the body; and (b) a magnetically closeable reed switch, with spaced apart reeds, mounted on the body adjacent the magnet and with an electrical connector to the reeds for connection to the dispensing means, wherein the reed switch or magnet are moveable relative to each other on the body, wherein upon the movement a magnetic field from the magnet closes the reed switch in one position of the movement to turn on the dispensing means and at another position of the movement the reed switch is opened away from the magnetic field of the magnet to turn off the dispensing means.

The present invention further provides a handheld syringe assembly for connection to an electrically powered dispensing means which reloads a liquid to be dispensed through a conduit by the syringe assembly through a disposable needle and hub assembly or hub, either mounted on the syringe assembly, after injecting a dose of the liquid which comprises (a) a body with a distal end and a proximal end and a passage along a longitudinal axis between the ends and with a stop on the distal end; (b) first attachment means, for removably attaching the hub of the disposable needle and hub assembly or the hub, mounted on the distal end of the body and second attachment means for connecting a conduit to the dispensing means; (c) a shield with a distal end and a proximal end mounted adjacent the distal end of the body and around at least a portion of the needle and hub, so that movement of the shield along the longitudinal axis on the body is limited by the stop between an extended position prior to the dispensing of the liquid and a collapsed position during the dispensing of the liquid; (d) a rod with a distal end and a proximal end mounted on the body parallel to the longitudinal axis so that the distal end of the rod engages a proximal end of the shield; (e) a permanent magnet creating a magnetic field mounted on the proximal end of the rod on the body parallel to the longitudinal axis with a coil spring which biases the magnet and rod into the engagement with the shield prior to and during the dispensing; (f) a magnetically actuatable reed switch mounted on the body so as to be moveable in proximity to the magnetic field which closes the read switch with spaced apart reeds with an electrical connector to the reeds for activating the electrically powered dispensing means; and (g) a cover over the body for holding the reed switch, coil spring, permanent magnet and rod on the body, wherein the movement of the magnet by the shield and rod means brings the magnet in proximity of the reed switch so that the reeds are closed to activate the dispensing means and the reeds are opened upon movement of the magnet and rod away from the reed switch.

In a further embodiment of the above handheld syringe assemblies, the dispensing means is a pump for a fluid. Preferably, the pump is a piston pump operated by a linear actuator to provide linear motion for the piston pump.

In a further embodiment, the linear actuator includes (a) a solenoid coil, with a linearly movable armature having a distal end and a proximal end, mounted on a support means, wherein the distal end of the armature is pulled into the solenoid coil when the solenoid is electrically activated and retracts automatically when the solenoid is electrically deactivated; (b) a piston removably connected to a push rod connected to the distal end of the armature for the linear movement of the push rod and the piston by the armature when the solenoid coil is electrically activated and deactivated; (c) a tubular member with a proximal end for confining the piston for the linear movement and a distal end; and (d) a connector on the distal end of the tubular member, with two channels, a first of the channels containing a one-way valve for filling the tubular member and the connector when the piston is retracted when the solenoid is deactivated and a second of the channels containing a second one-way valve which opens when the piston is advanced by the push rod when the solenoid is activated to dispense the fluid from the second of the channels to the syringe assembly.

In a further embodiment, the linear actuator includes (a) a solenoid coil, with a linearly movable armature having a distal end and a proximal end, mounted on a support means, wherein the distal end of the armature is pulled into the solenoid coil when the solenoid is electrically activated and retracts automatically when the solenoid is electrically deactivated; (b) a push rod connected to the distal end of the armature for the linear movement of the push rod by the armature when the solenoid coil is electrically actuated; (c) a tubular member with a proximal end for confining the push rod for the linear movement and a distal end; and (d) a one-way valve between the distal and proximal ends of the tubular member for filling the tubular member when the push rod is retracted when the solenoid is deactivated and a second one-way valve at the distal end of the tubular member which opens when the push rod is advanced by the armature when the solenoid is activated to dispense the fluid from the tubular member to the syringe.

The present invention further provides a pump for a fluid which comprises (a) a solenoid coil, with a linearly movable armature having a distal end and a proximal end, mounted on a support means, wherein the distal end of the armature is pulled into the solenoid coil when the solenoid is electrically activated and retracts automatically when the solenoid is electrically deactivated; (b) a piston removably connected to a push rod connected to the distal end of the armature for the linear movement of the push rod and the piston by the armature when the solenoid coil is electrically activated and deactivated; (c) a tubular member with a proximal end for confining the piston for the linear movement and a distal end; and (d) a connector on the distal end of the tubular member, with two channels, a first of the channels containing a one-way valve for filling the tubular member and the connector when the piston is retracted when the solenoid is deactivated and a second of the channels containing a second one-way valve which opens when the piston is advanced by the push rod when the solenoid is activated to dispense the fluid from the second of the channels.

The present invention further provides a pump for fluid which comprises (a) a solenoid coil, with a linearly movable armature having a distal end and a proximal end, mounted on a support means, wherein the distal end of the armature is pulled into the solenoid coil when the solenoid is electrically activated and retracts automatically when the solenoid is electrically deactivated; (b) a push rod connected to the distal end of the armature for the linear movement of the push rod by the armature when the solenoid coil is electrically actuated; (c) a tubular member with a proximal end for confining the push rod for the linear movement and a distal end; and (d) a one-way valve between the distal and proximal ends of the tubular member for filling the tubular member when the push rod is retracted when the solenoid is deactivated and a second one-way valve at the distal end of the tubular member which opens when the push rod is advanced by the armature when the solenoid is activated to dispense the fluid from the tubular member to the syringe.

The present invention further provides a system for a handheld syringe assembly for connection to an electrically powered dispensing means which reloads a liquid to be dispensed through a conduit by the syringe assembly through a disposable needle and hub assembly or hub, either mounted on the syringe assembly, after injecting a dose of the liquid which comprises (a) a body with a distal end and a proximal end and a passage along a longitudinal axis between the ends and with a stop on the distal end; (b) a first attachment means, for removably attaching the hub of the disposable needle and hub assembly or hub, mounted on the distal end of the body and second attachment means for connecting a conduit to the dispensing means; (c) a shield with a distal end and a proximal end mounted adjacent the distal end of the body and around at least a portion of the needle and hub, so that movement of the shield along the longitudinal axis on the body is limited by the stop between an extended position prior to the dispensing of the liquid and a collapsed position during the dispensing of the liquid; (d) a rod with a distal end and a proximal end mounted on the body parallel to the longitudinal axis so that the distal end of the rod engages a proximal end of the shield; (e) a permanent magnet creating a magnetic field mounted on the proximal end of the rod on the body parallel to the longitudinal axis with a coil spring which biases the magnet and rod into the engagement with the shield prior to and during the dispensing; (f) a magnetically actuatable reed switch mounted on the body so as to be moveable in proximity to the magnetic field which closes the read switch with spaced apart reeds with an electrical connector to the reeds for activating the electrically powered dispensing means; and (g) a cover over the body for holding the reed switch, coil spring, permanent magnet and rod on the body, wherein the movement of the magnet by the shield and rod means brings the magnet in proximity of the reed switch so that the reeds are closed to activate the dispensing means and the reeds are opened upon movement of the magnet and rod away from the reed switch.

The present invention further provides an improved method for inoculating a plurality of animals with a liquid with a handheld syringe assembly which electrically connects to an electrically powered dispensing means which reloads the liquid to be dispensed through a conduit to the syringe assembly through a disposable needle and hub assembly or hub, either mounted on a body of the syringe assembly, after injecting a dose of the liquid into one of the plurality of animals which comprises (a) providing the handheld syringe assembly with a permanent magnet mounted on the body, and a magnetically closeable reed switch, with spaced apart reeds, mounted on the body adjacent the magnet and with an electrical connector to the reeds for connection to the dispensing means, wherein the reed switch or magnet are moveable relative to each other on the body, and wherein upon the movement a magnetic field from the magnet closes the reed switch in one position of the movement to turn on the dispensing means and at another position of the movement the reed switch is opened away from the magnetic field of the magnet to turn off the dispensing means; and (b) inoculating the plurality of animals with the handheld syringe assembly.

The present invention further provides a method for inoculating a plurality of animals with a liquid which comprises (a) providing a handheld syringe assembly for connection to an electrically powered dispensing means which reloads a liquid to be dispensed through a conduit by the syringe assembly through a disposable needle and hub assembly or hub, either mounted on the syringe assembly, after injecting a dose of the liquid wherein the handheld syringe includes (1) a body with a distal end and a proximal end and a passage along a longitudinal axis between the ends and with a stop on the distal end; (2) a first attachment means, for removably attaching the hub of the disposable needle, mounted on the distal end of the body and second attachment means for connecting a conduit to the dispensing means; (3) a shield with a distal end and a proximal end mounted adjacent the distal end of the body and around at least a portion of the needle and hub, so that movement of the shield along the longitudinal axis on the body is limited by the stop between an extended position prior to the dispensing of the liquid and a collapsed position during the dispensing of the liquid; (4) a rod with a distal end and a proximal end mounted on the body parallel to the longitudinal axis so that the distal end of the rod engages a proximal end of the shield; (5) a permanent magnet creating a magnetic field mounted on the proximal end of the rod on the body parallel to the longitudinal axis with a coil spring which biases the magnet and rod into the engagement with the shield prior to and during the dispensing; (6) a magnetically actuatable reed switch mounted on the body so as to be moveable in proximity to the magnetic field which closes the read switch with spaced apart reeds with an electrical connector to the reeds for activating the electrically powered dispensing means; and (7) a cover over the body for holding the reed switch, coil spring, permanent magnet and rod on the body, wherein the movement of the magnet by the shield and rod means brings the magnet in proximity of the reed switch so that the reeds are closed to activate the dispensing means and the reeds are opened upon movement of the magnet and rod away from the reed switch; and (b) inoculating the plurality of animals with the handheld syringe assembly.

In a further embodiment of the above system and methods, the dispensing means is a pump for a fluid. Preferably, the pump is a piston pump operated by a linear actuator to provide linear motion for the piston pump.

In a further embodiment, the linear actuator includes (a) a solenoid coil, with a linearly movable armature having a distal end and a proximal end, mounted on a support means, wherein the distal end of the armature is pulled into the solenoid coil when the solenoid is electrically activated and retracts automatically when the solenoid is electrically deactivated; (b) a piston removably connected to a push rod connected to the distal end of the armature for the linear movement of the push rod and the piston by the armature when the solenoid coil is electrically activated and deactivated; (c) a tubular member with a proximal end for confining the piston for the linear movement and a distal end; and (d) a connector on the distal end of the tubular member, with two channels, a first of the channels containing a one-way valve for filling the tubular member and the connector when the piston is retracted when the solenoid is deactivated and a second of the channels containing a second one-way valve which opens when the piston is advanced by the push rod when the solenoid is activated to dispense the fluid from the second of the channels to the syringe assembly.

In a further embodiment, the linear actuator includes (a) a solenoid coil, with a linearly movable armature having a distal end and a proximal end, mounted on a support means, wherein the distal end of the armature is pulled into the solenoid coil when the solenoid is electrically activated and retracts automatically when the solenoid is electrically deactivated; (b) a push rod connected to the distal end of the armature for the linear movement of the push rod by the armature when the solenoid coil is electrically actuated; (c) a tubular member with a proximal end for confining the push rod for the linear movement and a distal end; and (d) a one-way valve between the distal and proximal ends of the tubular member for filling the tubular member when the push rod is retracted when the solenoid is deactivated and a second one-way valve at the distal end of the tubular member which opens when the push rod is advanced by the armature when the solenoid is activated to dispense the fluid from the tubular member to the syringe.

In a further embodiment of the above system and methods, the liquid is a vaccine and in an embodiment further still, the animals are birds.

Further still, the present invention provides a needle and hub assembly comprising (a) a needle with a distal end and a proximal end and a lumen extending therethrough wherein the distal end is beveled and the proximal end is secured to a hub comprising an elongated body with a chamber therein; and (b) a filament including a rod with a distal end and a proximal end with a head secured to the proximal end wherein the rod of the filament is slidably positioned in the needle lumen and the head of the filament is positioned in the chamber of the elongated body such that in a first position the head of the filament forms a seal with proximal end of the lumen of the needle to separate the chamber of the hub from the lumen of the needle and the distal end of the rod extends into bevel at the distal end of the lumen of the needle and in a second position the head of the filament is away from the proximal end of the lumen of the needle which opens the lumen of the needle to the chamber of the hub and the distal end of the rod of the filament no longer extends into the bevel at the distal end of the lumen of the needle.

In a further embodiment of the needle and hub assembly, the lumen of the needle further includes a hole opposite the bevel at the distal end of the needle.

The above handheld syringe is particularly useful for inoculating poultry, particularly inoculating the poultry by the wing web method using the above needle and hub assembly, because the filament prevents fluid from leaking from the needle between inoculations.

Objects

Therefore, the present invention provides an embodiment of an automatic repeater vaccinator which eliminates the continual hand motion required by the manual repeater syringes.

These and other objects of the present invention will become increasingly apparent with reference to the following drawings and preferred embodiments.

DETAILED DESCRIPTION OF THE INVENTION

All patents, patent applications, government publications, government regulations, and literature references cited in this specification are hereby incorporated herein by reference in their entirety. In case of conflict, the present description, including definitions, will control.

The present invention provides an automatic repeater vaccinator apparatus for dispensing predetermined volumes of a fluid such as vaccine and reloading after each volume of fluid is dispensed. The apparatus comprises a handheld syringe for dispensing the fluid, a flexible conduit for transferring the fluid from a dispensing means to the syringe, and a reservoir for providing the fluid to the dispensing means. The dispensing means is electrically activated by a magnetically closeable switch in the syringe, which enables a predetermined volume of the fluid to be dispensed from the syringe when the dispensing means is activated and reloading fluid from the reservoir to replace the volume of fluid which has been dispensed from the syringe when the dispensing means is deactivated.

Figure 2:
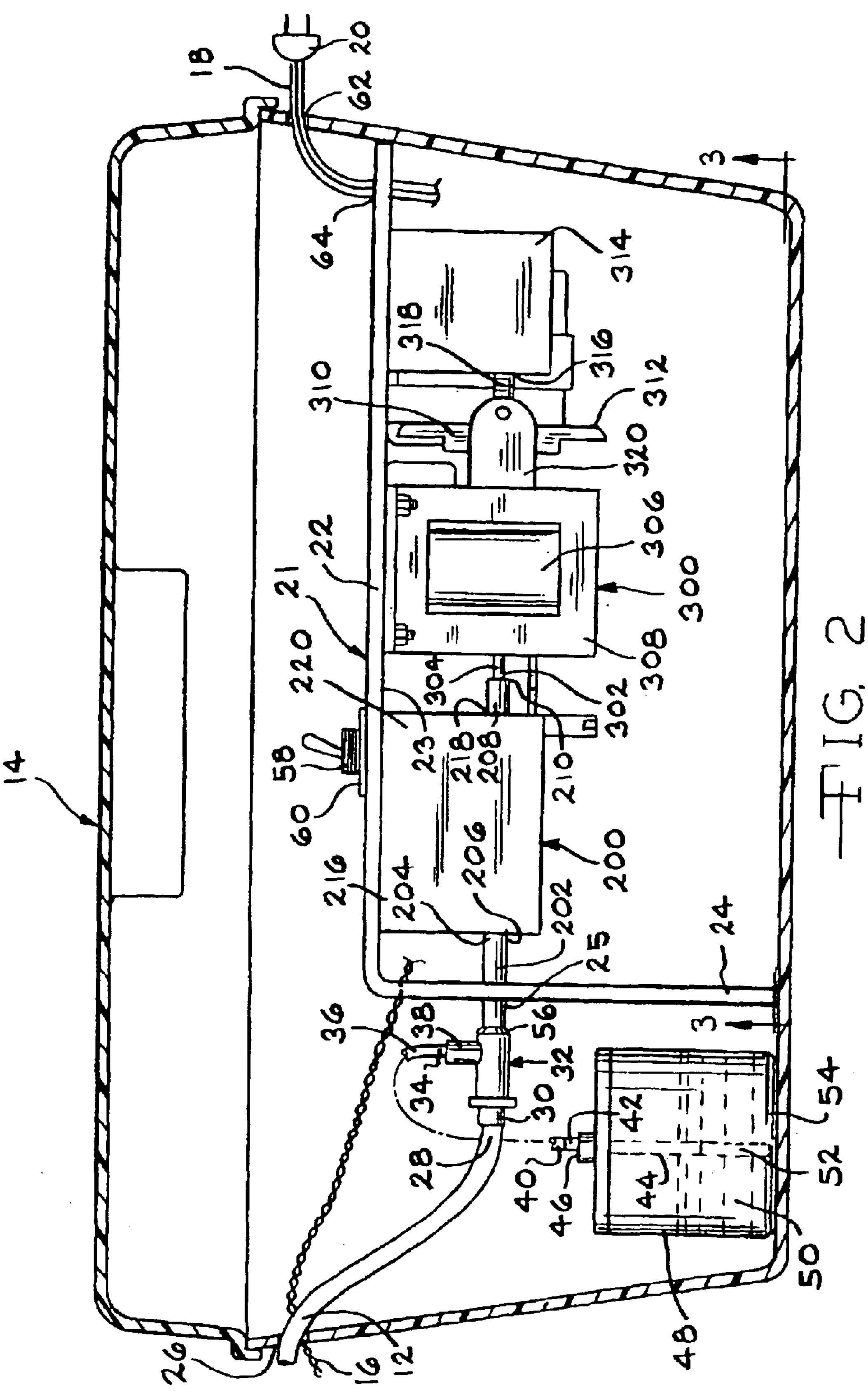
FIG. 2 shows a cross-section view of the container 14 along line 2—2 of FIG. 1 showing the piston pump 200 operated by the solenoid 300 and the reservoir 48 for the vaccine.
Figure 3:
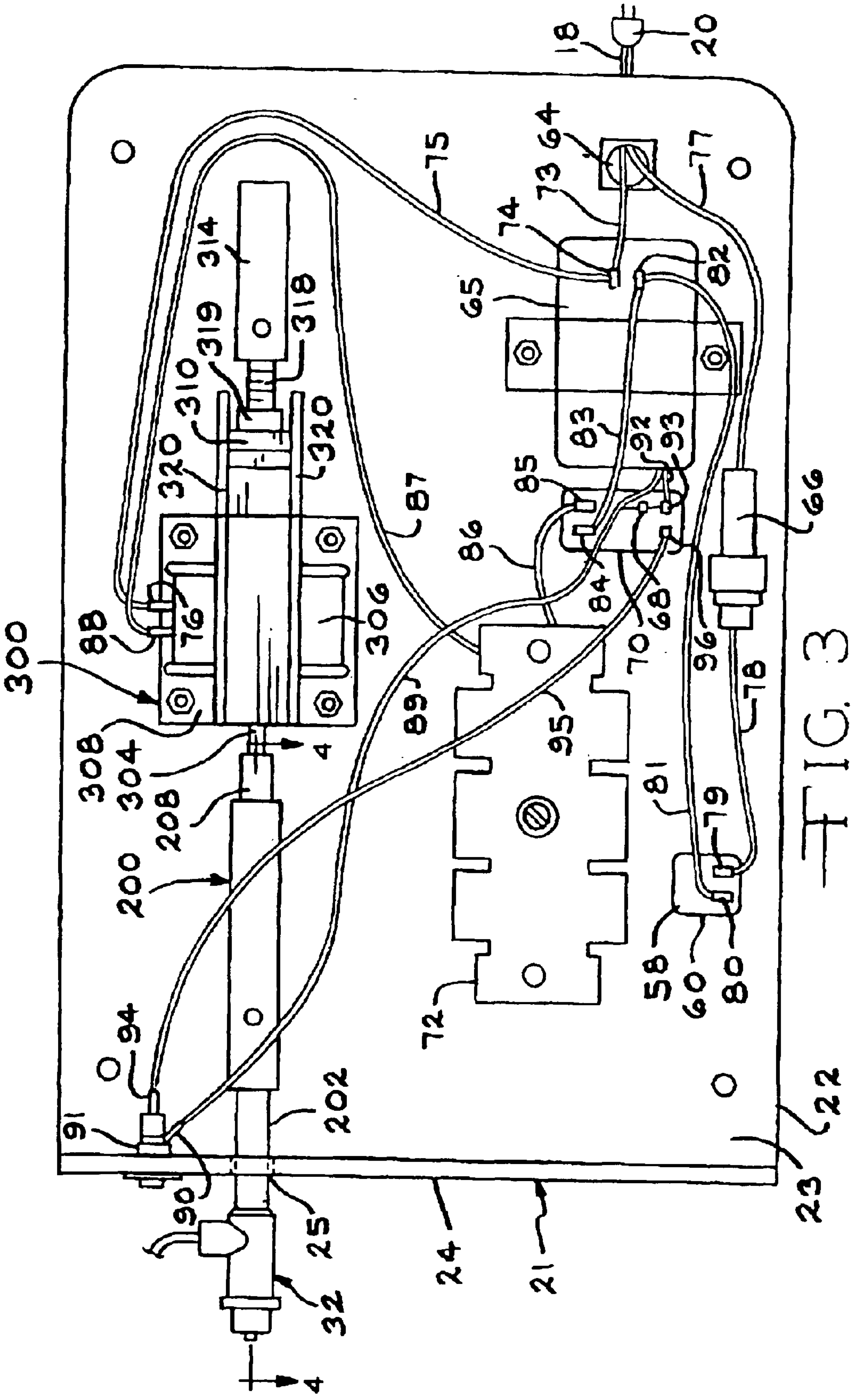
FIG. 3 shows a plan view of the container 14 along line 3—3 of FIG. 2 showing the piston pump 200 operated by the solenoid 300. Also shown is the transformer 65 for providing 6V DC current to the reed switch (not shown) in the syringe 100 (FIG. 1) and the relay 70 for controlling activation of the solenoid 300 by the circuit created when the reed switch is closed.

In a preferred embodiment, the dispensing means comprises a piston pump operated by a means for providing linear motion for operating the piston in the pump. Means for providing linear motion include linear actuators such as solenoids and non-solenoid linear actuators such as air cylinder linear actuators, rod linear actuators, rodless linear actuators, pneumatic linear actuators, and piezoelectric linear actuators. Linear actuators are available from numerous commercial sources including Haydon Switch and Instruments, Inc., Waterbury, Conn., and CK Design Technology, Simi Valley, Calif. Preferred non-solenoid linear actuators include those with a stepper motor and a screw rod as the shaft for operating the piston pump. Linear actuators which use a screw rod provide a linear motion which enables very precise volumes of fluid to be dispensed and reloaded. Alternatively, linear motion can be provided to the pump by a solenoid linear actuator as shown in FIGS. 2 to 3 and which is described in more detail below.

At one end of the syringe is a disposable needle and hub assembly with a retractable needle shield covering the disposable needle and hub assembly and at the other end of the syringe is an attachment means for the flexible conduit connecting the syringe to the pump and to the reservoir of fluid. The needle shield, which is operably connected to a permanent magnet, retracts when the needle is inserted into the skin of an animal. As the needle shield retracts, the magnet is moved to a position adjacent to the magnetically closeable switch which closes the switch. The closed switch completes an electric circuit that activates a solenoid or other linear actuator operating the pump which causes a predetermined volume of fluid to be dispensed from the syringe. When the needle is removed from the skin of the animal, the needle shield returns to a position covering the needle and hub assembly which moves the magnet to a position away from the magnetically closeable switch thereby opening the switch. The open switch breaks the electric circuit activating the solenoid or other linear actuator operating the pump which pulls fluid from the reservoir into the pump to replace the volume of fluid that had been dispensed from the syringe.

In a preferred embodiment, the magnetically closeable switch is a magnetically closeable reed switch and the pump comprising the dispensing means is a piston pump operated by a solenoid or other linear actuator. The preferred automatic repeater vaccinator apparatus comprising the piston pump operated by the solenoid or other linear actuator and the reed switch operates as follows. During use of the preferred vaccinator apparatus, the needle and hub assembly, the syringe, the flexible conduit connecting the syringe to the pump, the tubing from the reservoir to the pump, and the pump are completely filled with the fluid. When the needle shield covering the needle is pushed against the skin of an animal, the needle shield is pushed towards a retracted position enabling the needle to enter the skin. As the needle shield retracts, it pushes a rod with a magnet at the far end of the rod and which is biased against a coil spring to keep the rod engaged with the needle shield towards a reed switch. When the needle is fully inserted into the skin, the magnet at the far end of the rod is in a position adjacent to the reed switch. The magnet field of the magnet closes the spaced apart reeds comprising the reed switch which completes an electric circuit, preferably a low voltage circuit. The completed electric circuit activates a solenoid or other linear actuator which causes a piston in the pump controlled by the solenoid or other linear actuator to advance. The advancing piston in the pump creates a positive pressure which forces a volume of fluid proportional to the volume displaced by the advancing piston to be dispensed from the needle of the syringe into the skin of the animal.

Removing the needle from the skin breaks the electric circuit because in the absence of the external pressure of the skin against the needle shield, the needle shield returns to a position covering the needle and hub assembly by action of the coil spring biasing the rod with the magnet against the needle shield, which in turn pulls the magnet away from the reed switch. In the absence of the magnetic field of the magnet, the spaced apart reeds of the reed switch open thereby breaking the electric circuit. When the electric circuit is broken, the solenoid or other linear actuator is deactivated which causes the piston to return to its original position. The return of the piston to its original position produces a negative pressure that pulls a volume of fluid from the reservoir into the pump to replace the volume fluid that had been dispensed into the skin of the animal.

The automatic repeater vaccinator apparatus provides an improved means for inoculating a plurality of animals, particularly birds such as poultry, quickly and efficiently, and without requiring excessive hand movements by the operator which can lead to fatigue or injury. The novel elements of the apparatus include the magnetically closeable switch in the handheld syringe which is closed when the needle comprising the handheld syringe is inserted into an animal and which operates a solenoid or other linear actuator driving a pump to dispense the appropriate amount of fluid into the animal. It is further novel that the apparatus uses a solenoid or other linear actuator to produce positive pressure in the pump to dispense the fluid and negative pressure to reload the pump with the volume of fluid which had been dispensed.

The embodiment of the automatic repeater vaccinator illustrated by the Figures is intended to provide a further understanding of the operation of the invention. The embodiment shown in FIGS. 2, 3, 4, and 8 uses a solenoid to provide the linear motion for operating the piston pump. However, while the illustrated embodiment uses a solenoid to provide the linear motion, other embodiments of the automatic repeater vaccinator can include other means for providing the linear motion such as non-solenoid linear actuators, preferably those non-solenoid linear actuators which comprise a stepper motor and a screw as the shaft.

Figure 1:
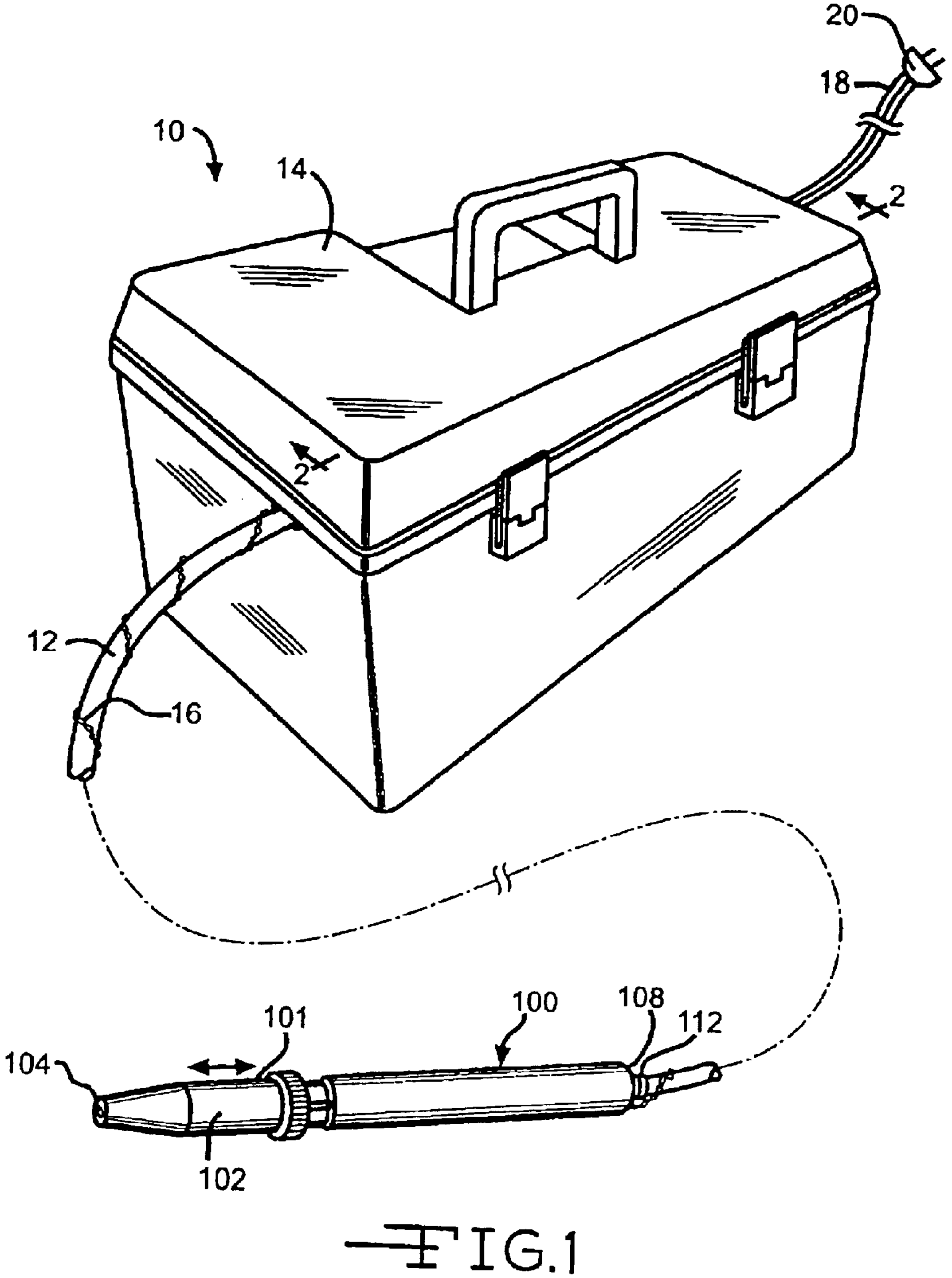
FIG. 1 shows an perspective view of the vaccinator apparatus 10 comprising the container 14 and syringe 100.

An overall view of a preferred automatic repeater vaccinator apparatus 10 for vaccinating an animal is shown in FIG. 1. Shown is a handheld syringe 100 with a retractable needle shield 102 and needle 104 of a disposable needle and hub assembly (148 in FIG. 6) at its distal end 101 and an attachment means 112 at its proximal end 108, which is connected to a flexible conduit 12 for carrying fluids such as vaccines, antibiotics, hormones, vitamins, nutraceuticals, and the like from the reservoir (48 in FIG. 2) in the container 14 to the syringe 100.

An electrical connector 16 operably provides 6V DC current to a magnetically closeable reed switch (142 of FIG. 6) in the syringe 100 which when in the closed position completes an electric circuit which activates a solenoid (300 in FIG. 2) in the container 14 that drives a piston pump (200 in FIG. 2). When the solenoid 300 is activated, the piston pump 200 pumps fluid through the flexible conduit 12 and the syringe 100 to the needle 104 in a predetermined dosage unit. Electric current to operate the syringe 100 and the solenoid 300 is provided to the vaccinator apparatus 10 through an electrical cord 18 with standard 110V DC outlet plug 20.

FIG. 2 shows a cross-section of the container 14 of the automatic repeater vaccinator apparatus 10 shown in FIG. 1 and shows the preferred dispensing means comprising a piston pump operated by a solenoid. The Figure shows within the container 14, support 21 comprising an upper wall 22 with a bottom surface 23 and a sidewall 24. The flexible conduit 12 for carrying the fluid enters the container 14 through the opening 26 and the proximal end 28 of the flexible conduit 12 is connected to the distal end 30 of a two-way connector 32. The proximal end 34 of a flexible tubing 36 for carrying fluid from a reservoir 48 to the two-way connector 32 is connected to an inlet 42 of the two-way connector 32 and the distal end 40 of the flexible tubing 36 is connected to the distal end 42 of a rigid tube 44. The rigid tube 44 extends through the opening 46 of the reservoir 48 containing fluid 50 to be injected into the animal using the syringe 100. Preferably, the proximal end 52 of the rigid tube 44 is in contact with the bottom 54 of the reservoir 48. The proximal end 56 of the two-way connector 32 is connected to piston pump 200 via a rigid tubular member 202.

The proximal end 204 of the tubular member 202 traverses the support 21 through opening 25 in the sidewall 24 and is inserted into the opening 206 of the pump chamber (214 in FIG. 4) located at the distal end 216 of the piston pump 200. The pump chamber 214 traverses the width of the piston pump 200 from the opening 206 at the distal end 216 to the opening 218 at the proximal end 220 of the piston pump 200. The piston pump 200 is secured to the lower surface 23 of the upper wall 22 of the support 21 by a securing means such as screws, bolts, welding, brackets, and the like. The piston pump 200 has a piston rod 208 which is inserted into the pump chamber 214 through the opening 218 at the proximal end 220 of the piston pump 200. The distal end 234 of the piston rod 208 is connected to the proximal end 232 of the piston (224 in FIG. 4). The piston 224 has a piston head (226 in FIG. 4) which is positioned within the tubular member 202 and which forms a seal with the wall (203 of FIG. 4) of the tubular member 202 to provide positive pressure on the fluid in the tubular member 202 when the solenoid 300 driving the piston pump 200 is activated and negative pressure when the solenoid driving the piston pump 200 is deactivated. The proximal end 210 of the piston rod 208 is connected to the distal end 302 of the push rod 304 the proximal end (not shown) of which is connected to the distal end (not shown) of the armature 310 of the solenoid 300 secured to lower surface 23 of the upper wall 22 of the support 21. The piston rod 208 and piston 224 move linearly within the pump chamber 214 of the piston pump 200 in response to activation or deactivation of the solenoid 300. Preferably, the piston 224, piston rod 208, and the push rod 304 connected at its proximal end to the distal end of the armature 310 are in linear alignment along the same longitudinal axis. However, in particular embodiments, the piston rod 208 and the push rod 304 can have an offset alignment along the longitudinal axis.

The solenoid 300 comprises coils 306 in a support 308 wherein the coils 306 form a central space (not shown) in which is positioned the armature 310 in which its distal end (not shown) is connected to the proximal end (not shown) of the push rod 304. The armature 310 is held in proper alignment in the central space of the solenoid 300 by guides 320. Positioned behind the proximal end 312 of the armature 310 is stop-block 314, which is secured to the lower surface 23 of the upper wall 22 of the support 21, and which has a threaded opening 316 for receiving an adjusting screw 318 with a head (319 in FIG. 3). The head 319 of the adjusting screw 318 rests against the proximal end 312 of the armature 310 when the solenoid 300 is deactivated. By adjusting the distance the head 319 of the adjusting screw 318 is from the stop block 314, the distance the armature 310 travels when the solenoid 300 is activated is correspondingly changed which in turn changes the volume of fluid dispensed from the needle 104 of the syringe 100. For example, as the head 319 is moved to a position closer to the stop block 314, the greater the distance the armature 310 travels when the solenoid 300 is activated. Thus, when the solenoid 300 is activated, the piston head 226 travels a greater distance within the tubular member 202 which in turn causes a greater volume of fluid to be dispensed from the needle 104 of the syringe 100. Conversely, as the head 319 is moved further from the stop block 314, the lesser the distance the armature 310 travels when the solenoid 300 is activated. Thus, the piston head 226 travels a lesser distance within the tubular member 202 which in turn causes a lesser volume of fluid to be dispensed from the needle 104 of the syringe 100. In the above manner, the volume of fluid to be dispensed from the needle 104 of the syringe 100 can be regulated. The solenoid 300 further includes a spring (not shown) therein which is compressed by the armature 310 when the solenoid 300 is activated and which causes the armature 310 to retract when the solenoid 300 is deactivated.

The two-way connector 32 contains a one-way flow valve (not shown) in the channel (not shown) at its distal end 30 and a one-way flow valve (not shown) in the channel (not shown) of the inlet 38. The one-way flow valves are designed such that when the solenoid 300 is activated, the armature 310 is pulled into the solenoid 300, which compresses the spring therein, and which causes the push rod 304 connected to the distal end of the armature 310 to move the piston rod 208 and piston 224 in the pump chamber 214 of the piston pump 200 from its rest position towards the direction of the two-way connector 32. This produces a positive pressure in the two-way connector 32 which closes the one-way valve in the inlet 38 and opens the one-way valve at the distal end 30 of the two-way connector 32. In this manner, activating the solenoid 300 causes the fluid in the system to be dispensed from the needle 104 of the syringe 100. When the solenoid 300 is deactivated, the push rod 304 connected to the distal end of the armature 310 retracts by action of the spring which pulls the piston rod 208 and piston 224 back to its resting position. This produces a negative pressure in the two-way connector 32 which causes the one-way valve at the distal end 30 of the two-way connector 32 to close and the one-way valve in the inlet 38 to open. When the one-way valve in the inlet 38 opens, fluid 50 is drawn from the reservoir 48 to replace the fluid which had been dispensed from the needle 104 of the syringe 100.

Electric current to operate the automatic repeater vaccinator apparatus 10 is controlled by switch 58 which traverses the opening 60 of the upper wall 22 of the support 21. Also shown is electrical cord 18 with plug 20 for providing 110V AC current to the automatic repeater vaccinator apparatus 10 which enters the container 14 through opening 62 and traverses the upper wall 22 of the support 21 through opening 64. 6V DC current to the syringe 100 is provided by electrical connector 16 which traverses the opening 26 in the container 14.

FIG. 3 is an overhead view of the bottom surface 23 of the upper wall 22 of the support 21 showing the various components comprising the automatic repeater vaccinator apparatus 10. FIG. 3 shows the alignment of the piston pump 200 to the solenoid 300 and shows the electrical connections between the power switch 58 for providing 110V AC electric current to the solenoid 300 and to a transformer 65 for providing 6V DC electric current to the magnetically closeable reed switch (142 in FIG. 6) in the syringe 100. Also shown in FIG. 3 is a fuse 66, a capacitor 68, a relay 70, and a variable resistance pot 72.

As further shown in FIG. 3, the neutral wire 73 of the electrical cord 18 carrying 110V AC current is connected to the neutral pole 74 of the transformer 65 and by wire 75 to the neutral pole 76 of the solenoid 300. The hot wire 77 of the electrical cord 18 is connected to fuse 66 which is then connected by wire 78 to the first pole 79 of the switch 58. When the switch 58 is in the closed (on) position, current travels from the second pole 80 along wire 81 to the hot pole 82 of the transformer 65 and by wire 83 to the first pole 84 of the relay 70. When the relay 70 is activated by the current flowing through the closed reed switch 142 in the syringe 100, the current travels from the second pole 85 of the relay 70 by wire 86 to the variable resistance pot 72, through the variable resistance pot 72, which enables the resistance to be adjusted, and then by wire 87 to the hot pole 88 of the solenoid 300.

The transformer 65 converts the 110V AC to 6V DC for operating the syringe 100. Wire 89 connects the transformer 65 to a first pole 90 of a panel connector 91 and from there a first wire (not shown) of the electrical connector 16 to one of the spaced apart reeds (144 in FIG. 6) of the reed switch 142. A second wire 92 from the transformer 65 is connected to a third pole 93 of the relay 70. The wire 89 and the second wire 92 are connected to each other by the capacitor 68 which smooths out voltage spikes in the circuit. When the spaced apart reeds 144 of the reed switch 142 are closed by the magnet 134, the 6V DC circuit is completed and current flows from the transformer 65, enters the relay 70 at the third pole 93 and exits the relay 70 at the fourth pole 96, travels along wire 95 to the second pole 94 of the panel connector 91 and along a second wire (not shown) of the electrical conductor 16 through the closed reed switch 142, back to the panel connector 91 along the first wire of the electrical connector 16, and from the first pole 90 of the panel connector 91 along wire 89 to the transformer 65. The completed 6V DC circuit activates the relay 70 which then completes the 110V AC circuit through poles 84 and 85 of the relay 70 thereby activating the solenoid 300.

Figure 4:
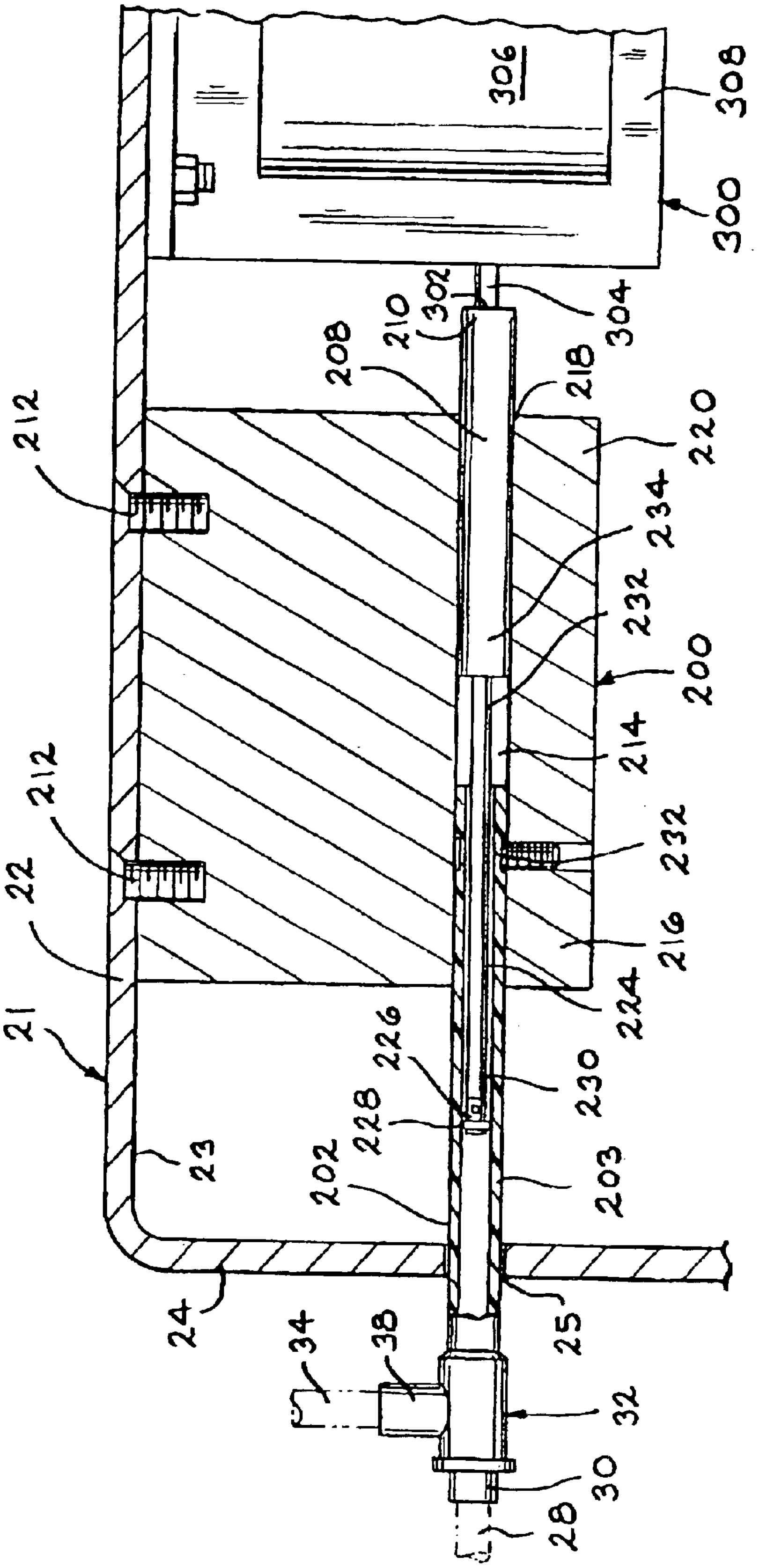
FIG. 4 shows cross-section view of the piston pump 200 along line 4—4 of FIG. 3.

FIG. 4 is a cross-section view of the piston pump 200. FIG. 3 shows an embodiment wherein the piston pump 200 is secured with machine screws 212 to the bottom surface 23 of the upper wall 22 of the support 21. The piston pump 200 comprises piston chamber 214 extending therethrough with opening 206 at the distal end 216 of the piston pump 200 and opening 218 at the proximal end 220 of the piston pump 200. The tubular member 202 extends through the opening 206 into the piston chamber 214 of the piston pump 200 and is held in place by the set screw 222. Seated within the tubular member 202 is the piston 224 with the piston head 226 with O-ring 228 attached thereto at the distal end 230 of the piston 224. The proximal end 232 of the piston 224 extends into the pump chamber 214 and is connected to the distal end 234 of the piston rod 208 which extends into the pump chamber 214 through opening 218. The proximal end 210 of the piston rod 208 is connected to the distal end 302 of the armature 304 of the solenoid 300.

Activation of the solenoid 300 causes the push rod 304 connected to the distal end of the armature 310 of the solenoid 300 to push the piston head 226 from its rest position towards the two-way connector 32. The positive pressure that is produced causes the one-way valve (not shown) in the distal end 30 of the two-way connector 32 to open and the one-way valve (not shown) in the inlet 38 to close so that the volume of fluid in the system displaced by the advancing piston 224 is dispensed from the needle 104 in the syringe 100. When the solenoid 300 is deactivated, the piston head 226 is pulled back to its resting position. The return motion causes a negative pressure which causes the one-way valve at the distal end 30 of the two-way connector 32 to close and the one-way valve in the inlet 38 to open thereby drawing from the reservoir 48 a volume of fluid to replace the volume of fluid which had been dispensed from the needle 104 of the syringe 100.

As can be seen by FIGS. 2, 3, and 4, the volume of fluid that can be dispensed can be adjusted by adjusting the distance the armature 310 travels in the solenoid 300 during activation. It is also apparent from the Figures that the volume of fluid can also be adjusted by concomitantly increasing the diameter of the tubular member 202 outside the pump 200 and the diameter of the piston head 226. Thus, the unit volume of fluid that can be dispensed is adjustable over a wide range of volumes and can used to inoculate small animals such as birds and poultry in particular or large animals such as pigs, cattle, and horses.

While a piston pump 200 is shown, the vaccinator apparatus 10 can use other pumps such as a peristaltic pump. When a pump such as a peristaltic pump is used, the elements shown remain the same except that the 110V AC current activates the pump directly since there is no need for the solenoid 300 to operate the pump.

Figure 5:
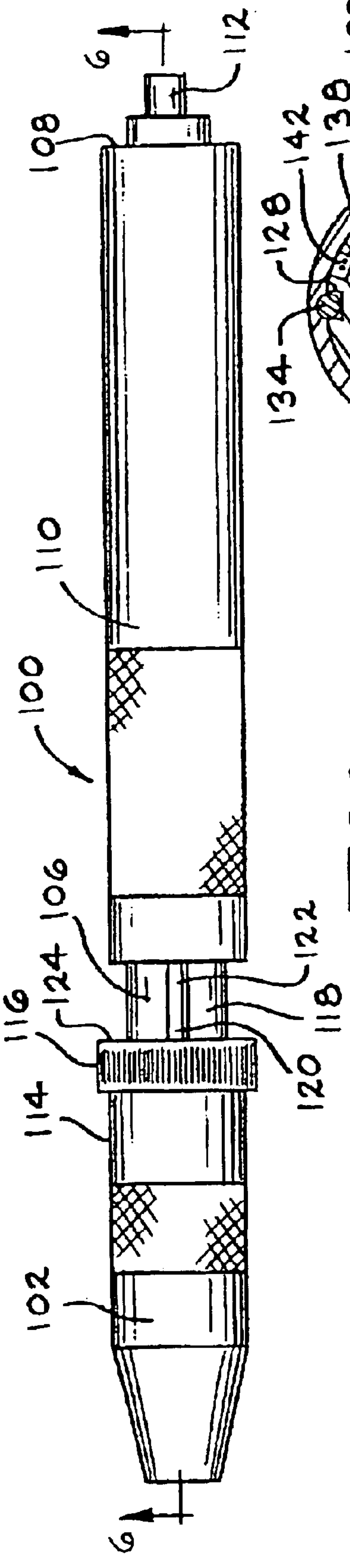
FIG. 5 shows a plan view of the syringe 100.

FIG. 5 shows a side view of the handheld syringe 100. The syringe 100 comprises a body (130 in FIG. 6) encased in a cover or sleeve 110, the body 130 further having a distal end 106 and a proximal end 108 and a slidable needle shield 102 covering a disposable needle and hub assembly (148 in FIG. 6) removably secured to the distal end 106 of the body by means of a luer lock. The proximal end 108 of the body has an attachment means 112, which can be a luer lock, for attaching the flexible conduit 12 to the syringe 100. Extending through the center of the body is a passage (166 in FIGS. 6 and 7 ) which is continuous with the flexible conduit 12 and the lumen (168 in FIG. 6) of the needle 104. The proximal end 114 of the needle shield 102 has internal threads (160 in FIG. 6) for securing the needle shield 102 to the external threads (162 in FIG. 6) on the neck (115 in FIG. 6) of the ring collar 116 which is mounted on the distal end 106 of the body 130. Also shown on the surface 118 of the distal end 106 of the body 130 is the distal end 120 of rod 122 which has at its proximal end (132 in FIG. 6), a magnet (134 in FIG. 6) for closing the magnetically closeable reed switch (142 in FIG. 6) when the magnet 134 is adjacent to the magnetically closeable reed switch 142. The distal end 120 of the rod 122 is adjacent to the proximal surface 124 of the ring collar 116.

In further embodiments of the handheld syringe, the depth the needle 104 penetrates the skin can be controlled by the length of the needle 104 that is exposed when the needle shield 102 is retracted, the length of the needle shield 102, by the distance the needle guard 102 is able to retract over the distal end 106 of the body 126, or combinations thereof.

Figure 7:
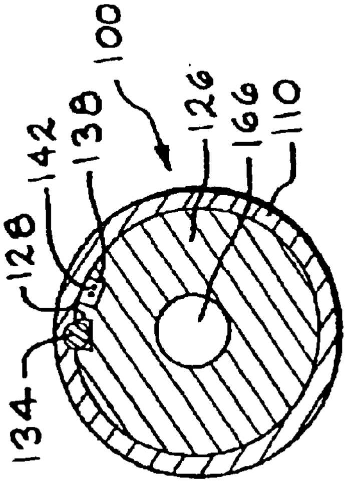
FIG. 7 shows a cross-section view of the syringe 100 along line 7—7 of FIG. 6.
Figure 6:
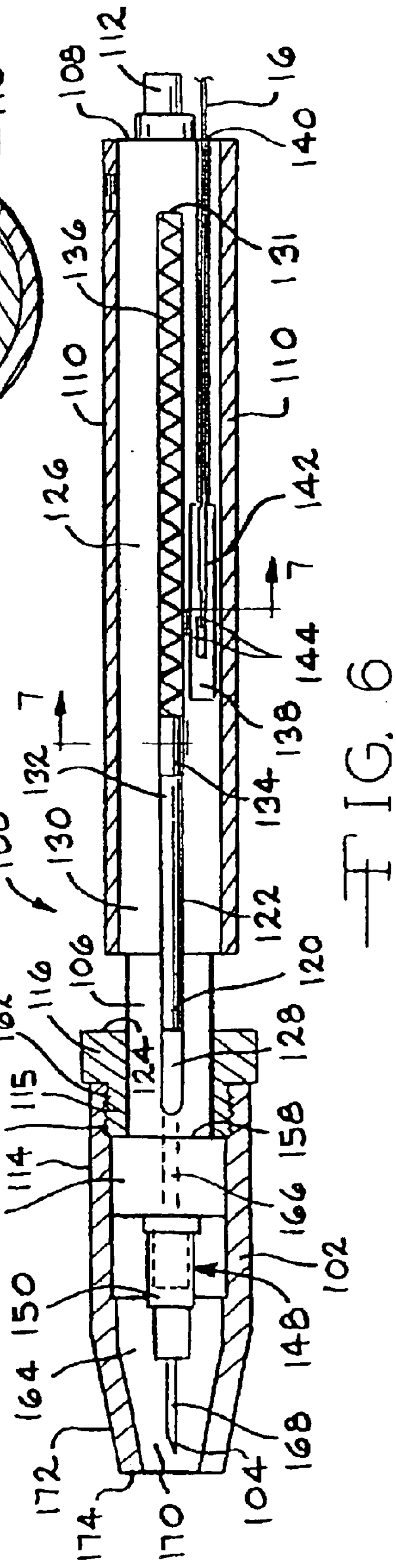
FIG. 6 shows a cross-section view of the syringe 100 along line 6—6 of FIG. 5.

The construction of the syringe 100 is more clearly shown in FIGS. 6 and 7. In FIG. 6, which is a cross-section along line 6—6 of FIG. 5, the body 126 is shown with a distal end 122 and a proximal end 108 with the attachment means 112 at the proximal end 108 for attaching the flexible conduit 12 to the body 126. The body 126 has a passage 166 extending parallel to the longitudinal axis of the body 126 and continuous to the lumen 168 of the needle 104 and an opening (not shown) in the attachment means 112. The diameter of the body 126 is greater than the diameter of the distal end 106 of the body 126 which enables the body 126 act as a stop when the needle shield 102 is retracted. Also shown is needle shield 102 with opening 170 and edge 174 at the distal end 172.

As shown in FIG. 6, a rod 122 resides within a groove 128 which is parallel to the longitudinal axis of the body 126 and extends along the surface 118 of the distal end 106 of the body 126 and then along the surface 130 of the body 126 to a position 131 within the proximal end 106 of the body 126. At the proximal end 132 of the rod 122 is a permanent magnet 134 which is adjacent to a coil spring 136 which biases the permanent magnet 134 and distal end 120 of the rod 122 into engagement with the proximal surface 124 of the ring collar 116 which is threadably connected to the needle shield 102. Adjacent to the groove 128 is a second groove 138 which is parallel to groove 128 and the longitudinal axis of the body 126 and which extends along the surface 130 of the body 126 to opening 140 at the proximal end 108 of the body 126. Residing within the second groove 138 is a magnetically closeable reed switch 142 with spaced apart reeds 144 operably connected to the relay 70 by electrical connector 16.

The magnetically closeable reed switch 142 is positioned in the second groove 138 so that only when the needle shield 102 is retracted is the permanent magnet 134 moved to a position adjacent to the reed switch 142. When the permanent magnet 134 is adjacent to the reed switch 142, the magnetic field of the permanent magnet 134 causes the spaced apart reeds 144 of the reed switch 142 to close (contact each other) thereby completing an electric circuit which activates the solenoid 300. The activated solenoid 300 causes the piston 224 in the piston pump 200 to advance a particular distance within the tubular member 202 of the piston pump 200 which causes a unit volume of fluid corresponding to the volume displaced by the advancing piston 224 to be dispensed from the needle 104. When the magnet 138 is moved away from the closed spaced apart reeds 144, the spaced apart reeds 144 separate which breaks the electric circuit and deactivates the solenoid pump 300. The deactivated solenoid 300 causes the piston 224 of the piston pump 200 to return to its resting position which produces a negative pressure that causes a volume of fluid equivalent to the volume of fluid dispensed from the syringe 100 to be pulled from the reservoir 48 into the tubular member 202 of the piston pump 200. The rod 122, permanent magnet 134, coil spring 136, and reed switch 142 are kept in the their respective grooves (128 and 138, respectively) by the sleeve 110 which fits around the body 126.

Even though other switches such as mechanical switches and the like can be used in the syringe 100, the reed switch 142 is preferred because the reed switch 142 has a considerably longer useful life than other switches. Ordinary mechanical switches have an average useful life of about 100,000 on-offs. Since about 10,000 birds are vaccinated per day, an ordinary mechanical switch would on average have to be replaced every ten days or so. The reed switch 142 has a useful life of about four to five million on-offs which enables it to last for about 400 to 500 days of continuous operation.

At the distal end 106 of the body 126 is shown the needle and hub assembly 148 comprising a needle 104 and hub 150 with external threads, preferably luer lock threads (not shown). An attachment means, preferably as shown herein, a luer lock collar 152 with internal luer lock threads (not shown) for receiving the external luer lock threads of the hub 150 is secured to the distal end 106 of the body 126. In an embodiment not shown, the luer lock collar 152 has at its proximal end 158 an elongated neck with threads which enables the luer lock collar 152 to be screwed into a threaded opening (not shown) at the distal end 106 of the body 126. The luer lock collar 152 has a diameter greater than the diameter of the distal end 106 of the body 126 which enables the proximal end 158 of the luer lock collar 152 to serve as a stop to prevent the ring collar 116 and needle shield 102 connected thereto from sliding off the distal end 106 of the body 126 because of the tension of the coil spring biasing the rod 122 into engagement with the ring collar 116. The needle shield 102 is threadably connected by internal threads 160 to the external threads 162 on the neck 115 of the ring collar 116. Further shown is passage 166 which is continuous with the lumen 168 in the needle 104 and passage (not shown) in the flexible conduit 12. In the rest position, the needle 104 is contained within the internal space 164 defined by the needle shield 102.

FIG. 7 shows a cross-section of the syringe 100 along line 7—7 of FIG. 6. FIG. 7 shows the body 126 encased by sleeve 110 and the passage 166 which extends parallel to the longitudinal axis the length of the body 126 to provide a passage for fluid to travel from the flexible conduit 12 to the lumen 168 of the needle 104. The Figure further shows the magnet 134 slidably located in the groove 128 and which is movable to a position adjacent to the reed switch 142 located in the second groove 138.

Figure 8:
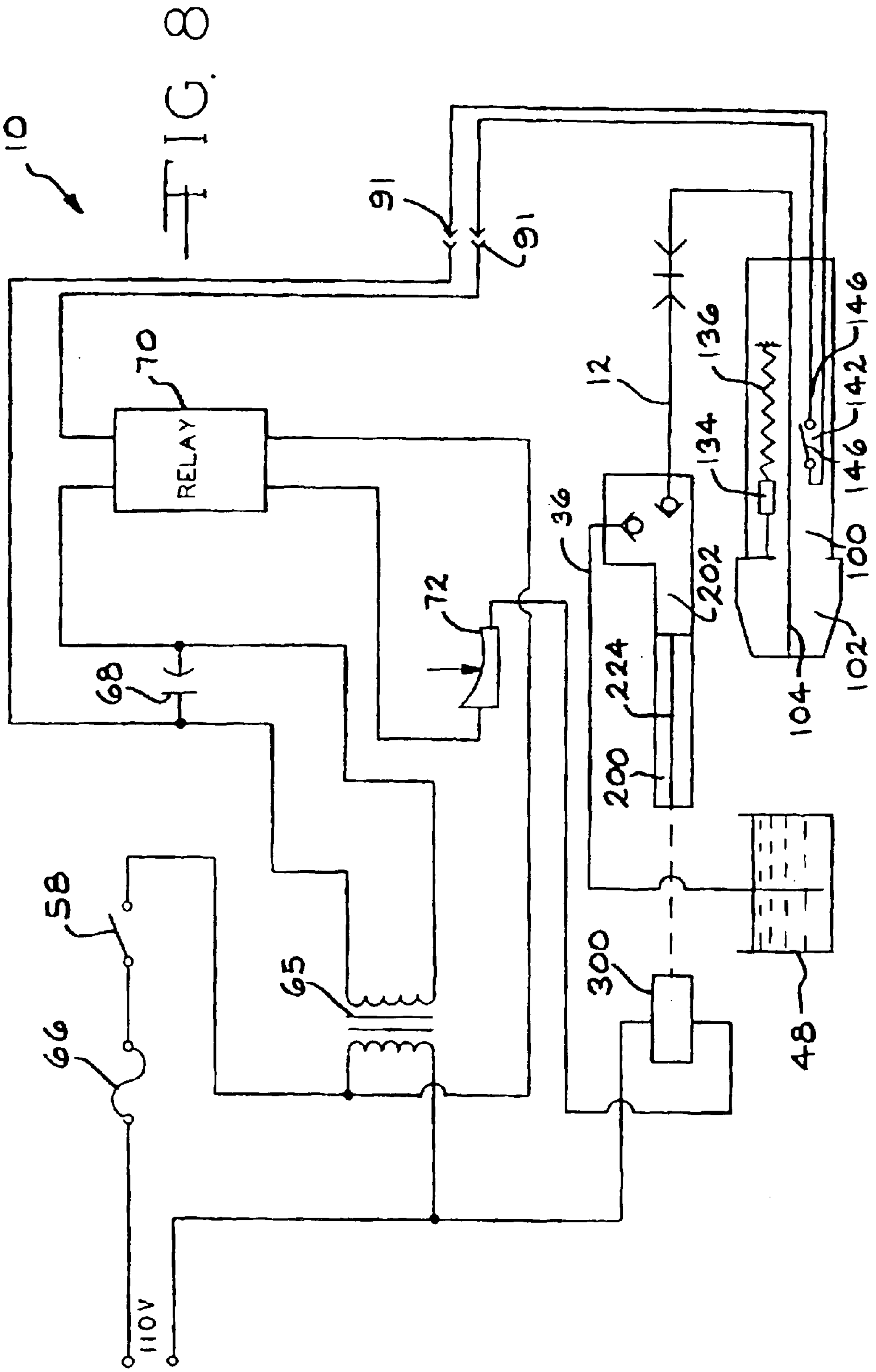
FIG. 8 shows a schematic diagram of the vaccinator apparatus 10.

FIG. 8 shows a schematic diagram of the vaccinator apparatus 10. 110 AC current to the vaccinator apparatus 10 is controlled by switch 58 and the circuit protected by fuse 66. When switch 58 is closed, current is provided to the vaccinator apparatus 10. In the closed position, 110V AC current is provided to the transformer 65 which converts the current to 6V DC current which is then routed to the reed switch 142 in the syringe 100. When the needle 104 is inserted into an animal, the needle shield 102 is pushed into a retracted position which also pushes the magnet 134 to a position adjacent to the reed switch 142. The magnetic field of the magnet 134 causes the spaced apart reeds 144 to close (in contact), thereby completing the 6V DC circuit. Also shown is the capacitor 68 (100uf35V) bridging the 6V DC current circuit at a point between the transformer 65 and the relay 70. When the 6V DC current in the closed circuit passes through the relay 70, the relay 70 closes the 110V AC circuit. The resistance of the current in the closed 110V AC circuit is adjusted using the variable resistance pot 72 and the resistance-adjusted 110V AC current activates the solenoid 300.

The solenoid 300 activates the piston pump 200 which produces a positive pressure that forces a volume of fluid corresponding to the volume of fluid displaced by the advancing piston 224 of the piston pump 200 through the flexible conduit 12 thereby causing a dose of fluid to be dispensed from the needle 104 of the syringe 100 corresponding to the volume of fluid displaced by the advancing piston 224. When the needle 104 is withdrawn from the animal, the magnet 134 is pushed away from the position adjacent to the reed switch 142 by the coil spring 136 which causes the needle shield 102 to return to its position covering the needle 104. When that happens, the spaced apart reeds 144 of the reed switch 142 are opened (out of contact) which breaks the 6V DC circuit. Because the 6V DC circuit is broken, the relay 70 opens the 100V AC circuit, which deactivates the solenoid 300, which causes the plunger 310 to retract, which in turn causes the piston 224 connected to it to retract thereby producing a negative pressure which causes fluid equivalent to the volume of fluid that was dispensed from the needle 104 to be pulled from the reservoir 48 into the tubular member 202 of the piston pump 200.

The vaccinator apparatus 10 is particularly useful for vaccinating poultry intraperitoneally, subcutaneously, or the like. Thus, the embodiment of the pump 200 illustrated in FIGS. 2, 3, and 4 is preferably used with the standard 0.5 inch long syringe needle and hub assemblies currently used for vaccinating poultry intraperitoneally, subcutaneously, or the like. For that embodiment, volumes of fluid from about 0.1 mL to about 0.75 mL are readily dispensed from the apparatus. Likewise, the embodiment shown in FIGS. 2, 3, and 4 can be modified by increasing the diameter of the tubular member 202 and piston rod head 226 to enable the vaccinator apparatus 10 shown be useful for vaccinating other livestock. Furthermore, in particular embodiments, the tubular member 202 is preferably disposable.

However, vaccinating poultry by the wing web method or the eye drop method uses far smaller volumes of fluid than is used by the above method. While proper adjustment of the travel of the piston rod head 226 in the tubular member 202 will enable very small volumes to be dispensed, it is preferable for wing web and eye drop vaccinations to use the vaccinator apparatus 10 with the modified pump 500 shown in FIG. 10 instead of the pump 200. Conceptually, the modified pump 500 combines the two-way valve 32, tubular member 202, and the piston pump 200 into a single unit (modified pump 500) and replaces the piston rod head 226 with the distal end of the push rod 304 that is connected to the distal end of the armature 310 of the solenoid 300. When the vaccinator apparatus 10 is fitted with the modified pump 500, preferably the variable resistance pot 72 shown in FIGS. 3 and 8 is not used.

Figure 10:
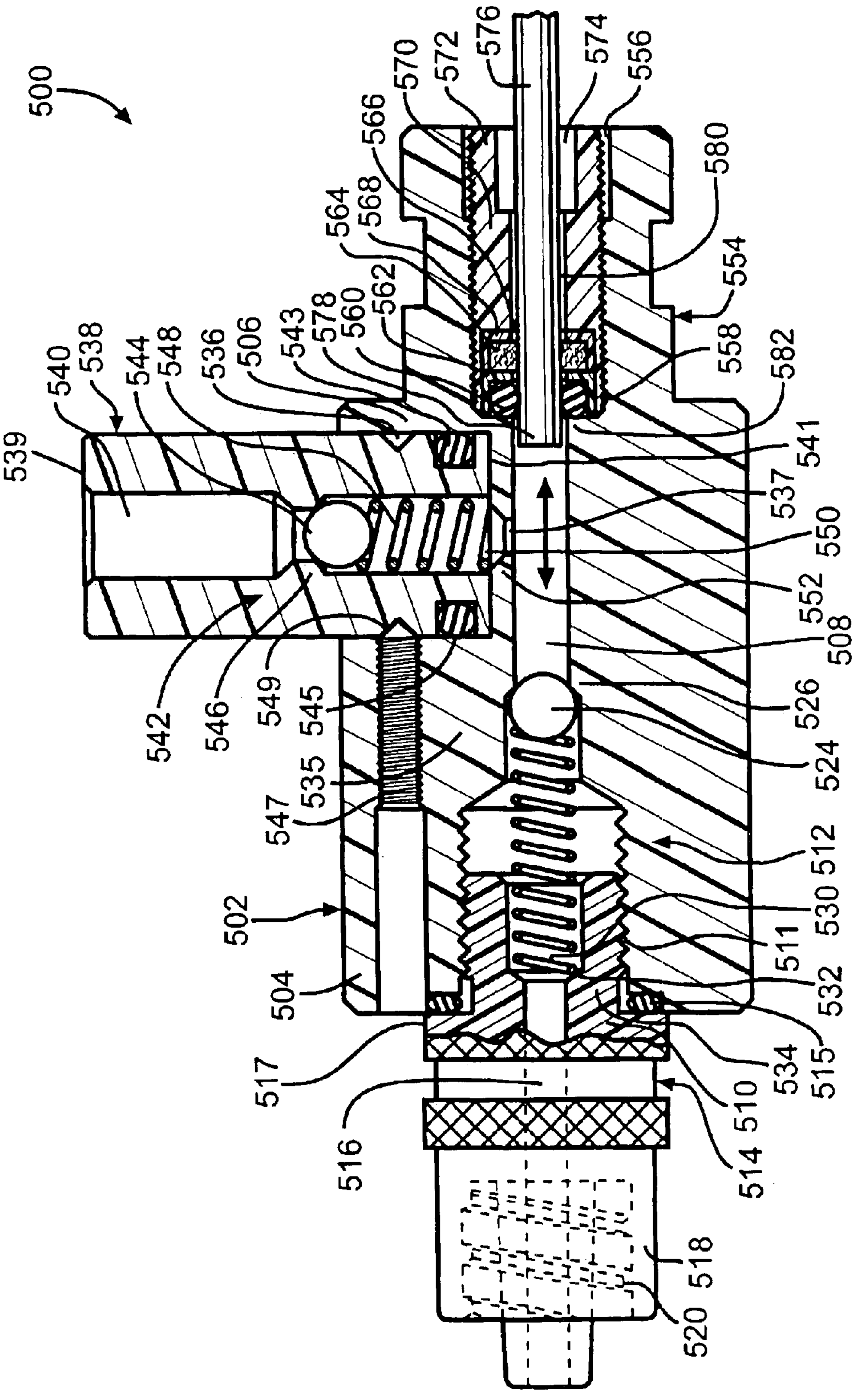
FIG. 10 shows a cross-section view of the modified pump 500 which is preferred for eye drop and wing web inoculations.

FIG. 10 shows the modified pump 500 which comprises a valve body 502 with a distal end 504 and a proximal end 506 and a chamber 508 extending therethrough. At the distal end 504 of the valve body 502 is an opening 510 with threads 511 for receiving the threaded end 512 of a hub 514 with a channel 516 extending therethrough and which has a standard luer lock collar 518 with internal luer lock threads 520. Also shown is O-ring 515 between proximal end 517 of the hub 514 and the distal end 504 of the valve body 502. The luer lock collar 518 enables the flexible conduit (not shown) to be connected to the modified pump 500 via a standard luer lock connection. Disposed within the chamber 508 of the valve body 502 is a first check valve 522 which is openable under positive pressure caused when the armature (not shown) of the activated solenoid (not shown) is pulled into the coils 306. The first check valve 522 comprises a ball 524 which in the absence of positive pressure is held against the stop 526 in the chamber 508 by the spring 528. The distal end 530 of the spring 528 rests against a stop 532 at the proximal end 534 of the hub 514.

Under positive pressure, fluid in the chamber 508 causes the spring 528 holding the ball 524 against the stop 526 in the chamber 508 to compress which enables fluid in the chamber 508 to pass into the channel 516 in the hub 514 and on down through the flexible conduit to the syringe (not shown). Under negative pressure and in the absence of positive or negative pressure, the ball 524 is held against the stop 526 in the chamber 508 by the spring 528 which prevents fluid from passing to the syringe or vice versa.

At a position between the first check value 510 and the proximal end 506 of the valve body 502 is a cavity 536 in the side wall 535 of the valve body 502 for receiving a second body 538 which has a channel 540 extending therethrough. The channel 540 is continuous with the opening 537 at the base 541 of the cavity 536 which leads to the chamber 508. The second body 538 is connectable at its distal end 539 to flexible tubing (not shown) which leads to the reservoir (not shown). The flexible tubing can be attached to the second body 538 by a luer lock or other means. Disposed within the channel 540 is a second check valve 542 which is openable under negative pressure caused as the armature of the deactivated solenoid retracts. The second check valve 542 comprises a ball 544 which in the absence of negative pressure is held against the stop 546 in the channel 540 by the spring 548. The distal end 550 of the spring 548 rests against a stop 552 formed by the base 541 of the cavity 536. Negative pressure causes the spring 548 holding the ball 544 to compress which enables fluid from the reservoir to pass into the chamber 508. Under positive pressure and in the absence of positive or negative pressure, the ball 544 is held against the stop 546 by the spring 548 which prevents fluid from passing from the reservoir to the chamber 508 or vice versa.

An O-ring 543 in a groove 545 of the second body 538 is used to provide a seal which prevents fluid leaks. A set screw 547 which engages a second groove 549 in the second body 538 keeps the second body 538 properly positioned in the cavity 536.

At the proximal end 506 of the valve body 502 is a neck 554 with threaded opening 556 which has a diameter greater than the diameter of the chamber 508 of the valve body 502. Disposed at the distal end 558 of the opening 556 is an O-ring 560 held in position by bracket 562 and felt pad 564 with opening 566 held in position by second bracket 568. The brackets 562 and 568 are held in place by set screw 570 which has a hex screw head 572 and channel 574 extending therethrough. Extending through the channel 574 is a push rod 576 with a distal end 578, which serves as the piston for the modified pump 500, and a proximal end (not shown) which is connected to the distal end (not shown) of the armature of the solenoid 300. The distal end 578 of the push rod 576 extends through the channel 574 and into the chamber 508 of the valve body 502.

The surface 580 of the push rod 576 and the O-ring 560 form a seal which prevents fluid from leaking out of the chamber 508 of the valve body 508. The felt pad 564 has lubricant infused therein which lubricates the surface 580 of the push rod 576 as it reciprocates past the felt pad 564 in response to activation/deactivation of the solenoid and facilitates the formation of the seal between the O-ring 560 and the surface 580 of the push rod 576. The O-ring 560 is compressed between the stop 582 formed by the junction of the chamber 508 and the threaded opening 556 and the bracket 562.

When the chamber 508 has a diameter of about 0.105 inches and the push rod 576 has a diameter of about 0.093 inches, the modified pump 500 can be adjusted to dispense volumes of fluid from about 0.01 mL to about 0.03 mL. In contrast, the pump 200 can be adjusted to dispense volumes of fluid from about 0.1 mL to about 0.75 mL.

For eye drop inoculations, a hub without the needle (not shown) is secured to the distal end 106 of the body 126 instead of the needle and hub assembly 148 shown in FIG. 6. The opening 170 at the distal end 172 of the needle shield 102 is of sufficient diameter such that the edge 174 at the distal end 172 of the needle shield 102 surrounds the eye ball. Therefore, for eye drop inoculations, the edge 174 of the needle shield 102 is positioned over the eye region of the bird to surround the eye ball. Pressing the needle shield 102 against the surface of the eye region causes the needle shield 102 to retract as described previously; however, the hub is not exposed beyond the edge 174 of the needle shield 102. Thus, the hub does not come in contact with surface of the eye. In the retracted position, the modified pump 502 is activated and a drop forms at the end of the hub which is then dispensed into the eye ball. After the drop is dispensed to the eye ball, the syringe 100 is removed and the needle shield 102 resumes it rest position which deactivates the modified pump 502 which causes fluid to be drawn from the reservoir to replace the fluid which had been dispensed.

Figure 9A:
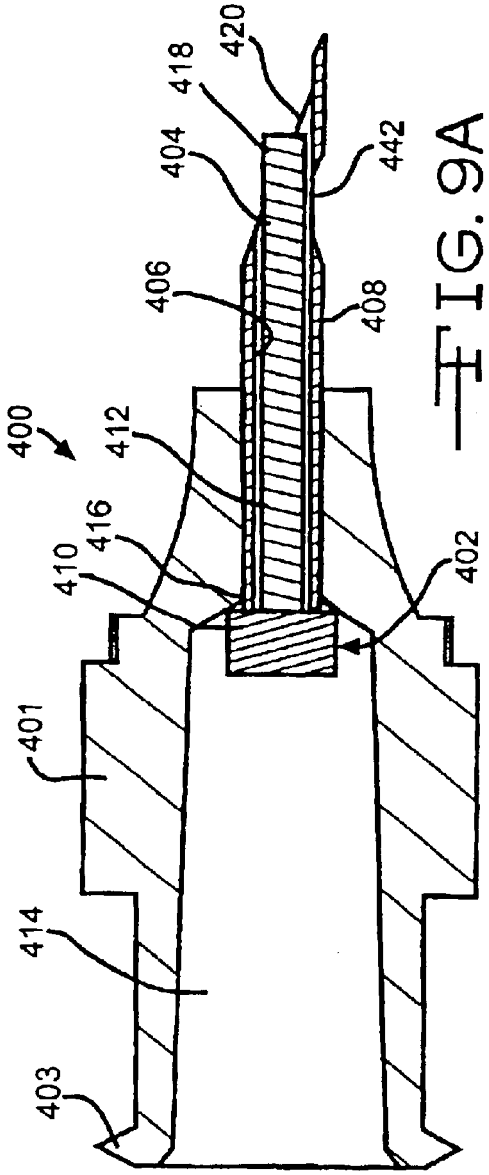
FIG. 9A shows a cross-section view of a needle and hub assembly 400 with the filament 402 in the closed position.
Figure 9B:
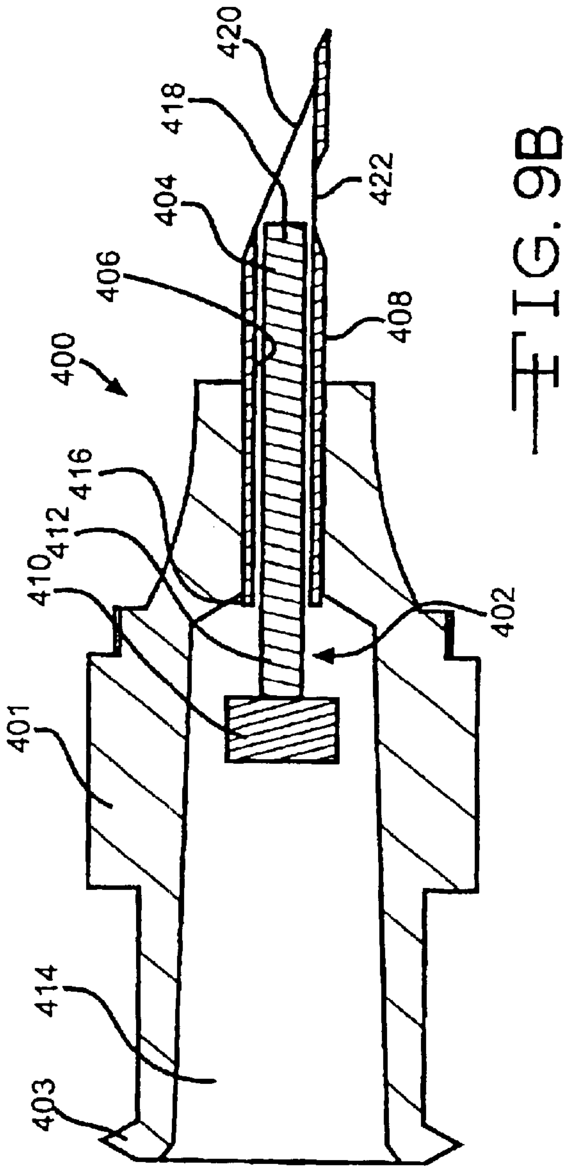
FIG. 9B shows a cross-section view of the needle and hub assembly 400 of FIG. 9A with the filament 402 in the open position.

For wing web inoculations, a needle and hub assembly suitable for wing web inoculations is secured to the distal end 106 of the body 126. In one embodiment, the novel wing web needle and hub assembly 400 shown in FIGS. 9A and 9B is preferred. FIGS. 9A and 9B shows the needle and hub assembly 400 for wing web vaccinations which comprises a needle 408 with a beveled area 420 at the distal end 421 and secured to the proximal end 416 of the needle 408, a hub 401 with a chamber 414 and external luer lock thread 403 to secure the needle and hub assembly 400 to the luer lock collar 152 of the syringe 100. The lumen 406 of the needle 408 is continuous with the chamber 414 in the hub 401. The needle further includes a back hole 422 which enables the vaccine to be dispensed over a range of 360° at the inoculation site.

As the needle 408 is inserted into the wing web, the tissue at the inoculation site urges the distal end 418 of the rod 404 of the filament 402 into the lumen 406 of the needle 408 which pushes the filament head 410 into the chamber 414 thereby allowing vaccine from the chamber 414 to enter the lumen 406 and to be dispensed into the wing web. Because the lumen 406 is greatly restricted by the diameter of the rod 404 of the filament 402, the filament 402 prevents the vaccine from spurting out of the needle 408 when the needle 408 is inserted into the wing web. Instead, the vaccine weeps out of the needle 408 in a 360° radius around the needle 408. Thus, the filament 402 acts both as a valve between vaccinations to prevent vaccine from leaking from the needle and hub assembly 400 and as a wick, which during vaccinations, prevents vaccine from spurting from the needle 408.

While the present invention is described herein with reference to illustrated embodiments, it should be understood that the invention is not limited hereto. Those having ordinary skill in the art and access to the teachings herein will recognize additional modifications and embodiments within the scope thereof. Therefore, the present invention is limited only by the claims attached herein.

I claim:

1. In a handheld syringe assembly which electrically connects to an electrically powered dispensing means which reloads a liquid to be dispensed through a conduit to the syringe assembly either through (I) a disposable needle and hub assembly or (ii) a hub, mounted on a body of the syringe assembly, after injecting a dose of the liquid, the improvement which comprises:

(a) a permanent magnet mounted on the body; and (b) a magnetically closeable reed switch, with spaced apart reeds, mounted on the body adjacent the magnet and with an electrical connector to the reeds for connection to the dispensing means, wherein the reed switch or magnet are moveable relative to each other on the body, wherein upon the movement a magnetic field from the magnet closes the reed switch in one position of the movement to turn on the dispensing means and at another position of the movement the reed switch is opened away from the magnetic field of the magnet to turn off the dispensing means.

2. The handheld syringe assembly of claim 1 wherein the dispensing means is a pump for a fluid.

3. The handheld syringe assembly of claim 2 wherein the pump is a piston pump operated by a linear actuator to provide linear motion for the piston pump.

4. The handheld syringe assembly of claim 3 wherein the linear actuator includes (a) a solenoid coil, with a linearly movable armature having a distal end and a proximal end, mounted on a support means, wherein the distal end of the armature is pulled into the solenoid coil when the solenoid is electrically activated and retracts automatically when the solenoid is electrically deactivated;

(b) a piston removably connected to a push rod connected to the distal end of the armature for the linear movement of the push rod and the piston by the armature when the solenoid coil is electrically activated and deactivated;

(c) a tubular member with a proximal end for confining the piston for the linear movement and a distal end; and (d) a connector on the distal end of the tubular member, with two channels, a first of the channels containing a one-way valve for filling the tubular member and the connector when the piston is retracted when the solenoid is deactivated and a second of the channels containing a second one-way valve which opens when the piston is advanced by the push rod when the solenoid is activated to dispense the fluid from the second of the channels to the syringe assembly.

5. The handheld syringe assembly of claim 3 wherein the linear actuator includes (a) a solenoid coil, with a linearly movable armature having a distal end and a proximal end, mounted on a support means, wherein the distal end of the armature is pulled into the solenoid coil when the solenoid is electrically activated and retracts automatically when the solenoid is electrically deactivated;

(b) a push rod connected to the distal end of the armature for the linear movement of the push rod by the armature when the solenoid coil is electrically actuated;

(c) a tubular member with a proximal end for confining the push rod for the linear movement and a distal end; and (d) a one-way valve between the distal and proximal ends of the tubular member for filling the tubular member when the push rod is retracted when the solenoid is deactivated and a second one-way valve at the distal end of the tubular member which opens when the push rod is advanced by the armature when the solenoid is activated to dispense the fluid from the tubular member to the syringe.

6. A handheld syringe assembly for connection to an electrically powered dispensing means which reloads a liquid to be dispensed through a conduit by the syringe assembly either through (I) a disposable needle and hub assembly or (ii) a hub, mounted on the syringe assembly, after injecting a dose of the liquid which comprises:

(a) a body with a distal end and a proximal end and a passage along a longitudinal axis between the ends and with a stop on the distal end;

(b) first attachment means, for removably attaching the hub of the disposable needle and hub assembly or hub, mounted on the distal end of the body and second attachment means for connecting a conduit to the dispensing means;

(c) a shield with a distal end and a proximal end mounted adjacent the distal end of the body and around at least a portion of the needle and hub, so that movement of the shield along the longitudinal axis on the body is limited by the stop between an extended position prior to the dispensing of the liquid and a collapsed position during the dispensing of the liquid;

(d) a rod with a distal end and a proximal end mounted on the body parallel to the longitudinal axis so that the distal end of the rod engages a proximal end of the shield;

(e) a permanent magnet creating a magnetic field mounted on the proximal end of the rod on the body parallel to the longitudinal axis with a coil spring which biases the magnet and rod into the engagement with the shield prior to and during the dispensing;

(f) a magnetically actuatable reed switch mounted on the body so as to be moveable in proximity to the magnetic field which closes the read switch with spaced apart reeds with an electrical connector to the reeds for activating the electrically powered dispensing means; and (g) a cover over the body for holding the reed switch, coil spring, permanent magnet and rod on the body, wherein the movement of the magnet by the shield and rod means brings the magnet in proximity of the reed switch so that the reeds are closed to activate the dispensing means and the reeds are opened upon movement of the magnet and rod away from the reed switch.

7. The handheld syringe assembly of claim 5 wherein the dispensing means is a pump for a fluid.

8. The handheld syringe assembly of claim 7 wherein the pump is a piston pump operated by a linear actuator to provide linear motion for the piston pump.

9. The handheld syringe assembly of claim 8 wherein the linear actuator includes (a) a solenoid coil, with a linearly movable armature having a distal end and a proximal end, mounted on a support means, wherein the distal end of the armature is pulled into the solenoid coil when the solenoid is electrically activated and retracts automatically when the solenoid is electrically deactivated;

(b) a piston removably connected to a push rod connected to the distal end of the armature for the linear movement of the push rod and the piston by the armature when the solenoid coil is electrically activated and deactivated;

(c) a tubular member with a proximal end for confining the piston for the linear movement and a distal end; and (d) a connector on the distal end of the tubular member, with two channels, a first of the channels containing a one-way valve for filling the tubular member and the connector when the piston is retracted when the solenoid is deactivated and a second of the channels containing a second one-way valve which opens when the piston is advanced by the push rod when the solenoid is activated to dispense the fluid from the second of the channels to the syringe assembly.

10. The handheld syringe assembly of claim 8 wherein the linear actuator includes (a) a solenoid coil, with a linearly movable armature having a distal end and a proximal end, mounted on a support means, wherein the distal end of the armature is pulled into the solenoid coil when the solenoid is electrically activated and retracts automatically when the solenoid is electrically deactivated;

(b) a push rod connected to the distal end of the armature for the linear movement of the push rod by the armature when the solenoid coil is electrically actuated;

(c) a tubular member with a proximal end for confining the push rod for the linear movement and a distal end; and (d) a one-way valve between the distal and proximal ends of the tubular member for filling the tubular member when the push rod is retracted when the solenoid is deactivated and a second one-way valve at the distal end of the tubular member which opens when the push rod is advanced by the armature when the solenoid is activated to dispense the fluid from the tubular member to the syringe.

11. A system for a handheld syringe assembly for connection to an electrically powered dispensing means which reloads a liquid to be dispensed through a conduit by the syringe assembly either through (I) a disposable needle and hub assembly or (ii) a hub, mounted on the syringe assembly, after injecting a dose of the liquid which comprises:

(a) a body with a distal end and a proximal end and a passage along a longitudinal axis between the ends and with a stop on the distal end;

(b) a first attachment means, for removably attaching the hub of the disposable needle and hub assembly or hub, mounted on the distal end of the body and second attachment means for connecting a conduit to the dispensing means;

(c) a shield with a distal end and a proximal end mounted adjacent the distal end of the body and around at least a portion of the needle and hub, so that movement of the shield along the longitudinal axis on the body is limited by the stop between an extended position prior to the dispensing of the liquid and a collapsed position during the dispensing of the liquid;

(d) a rod with a distal end and a proximal end mounted on the body parallel to the longitudinal axis so that the distal end of the rod engages a proximal end of the shield;

(e) a permanent magnet creating a magnetic field mounted on the proximal end of the rod on the body parallel to the longitudinal axis with a coil spring which biases the magnet and rod into the engagement with the shield prior to and during the dispensing;

(f) a magnetically actuatable reed switch mounted on the body so as to be moveable in proximity to the magnetic field which closes the read switch with spaced apart reeds with an electrical connector to the reeds for activating the electrically powered dispensing means; and (g) a cover over the body for holding the reed switch, coil spring, permanent magnet and rod on the body, wherein the movement of the magnet by the shield and rod means brings the magnet in proximity of the reed switch so that the reeds are closed to activate the dispensing means and the reeds are opened upon movement of the magnet and rod away from the reed switch.

12. The system of claim 11 wherein the dispensing means is a pump for a fluid.

13. The system of claim 12 wherein the pump is a piston pump operated by a linear actuator to provide linear motion for the piston pump.

14. The system of claim 13 wherein the linear actuator includes (a) a solenoid coil, with a linearly movable armature having a distal end and a proximal end, mounted on a support means, wherein the distal end of the armature is pulled into the solenoid coil when the solenoid is electrically activated and retracts automatically when the solenoid is electrically deactivated;

(b) a piston removably connected to a push rod connected to the distal end of the armature for the linear movement of the push rod and the piston by the armature when the solenoid coil is electrically activated and deactivated;

(c) a tubular member with a proximal end for confining the piston for the linear movement and a distal end; and (d) a connector on the distal end of the tubular member, with two channels, a first of the channels containing a one-way valve for filling the tubular member and the connector when the piston is retracted when the solenoid is deactivated and a second of the channels containing a second one-way valve which opens when the piston is advanced by the push rod when the solenoid is activated to dispense the fluid from the second of the channels to the syringe assembly.

15. The system of claim 13 wherein the linear actuator includes (a) a solenoid coil, with a linearly movable armature having a distal end and a proximal end, mounted on a support means, wherein the distal end of the armature is pulled into the solenoid coil when the solenoid is electrically activated and retracts automatically when the solenoid is electrically deactivated;

(b) a push rod connected to the distal end of the armature for the linear movement of the push rod by the armature when the solenoid coil is electrically actuated;

(c) a tubular member with a proximal end for confining the push rod for the linear movement and a distal end; and (d) a one-way valve between the distal and proximal ends of the tubular member for filling the tubular member when the push rod is retracted when the solenoid is deactivated and a second one-way valve at the distal end of the tubular member which opens when the push rod is advanced by the armature when the solenoid is activated to dispense the fluid from the tubular member to the syringe.

16. The system of claim 11 wherein the liquid is a vaccine.

* * * * *